United States Patent [19]

Novotny et al.

[11] Patent Number: 5,310,682

[45] Date of Patent: May 10, 1994

[54] FLUOROGENIC REAGENTS FOR DETECTION OF GLYCOCONJUGATES, α-KETOACIDS AND DIKETONES

[75] Inventors: Milos V. Novotny, Bloomington, Ind.; Osamu Shirota, Yokohama, Japan; Donald Wiesler, Bloomington, Ind.

[73] Assignee: Indiana University Foundation, Bloomington, Ind.

[21] Appl. No.: 900,207

[22] Filed: Jun. 17, 1992

[51] Int. Cl.$^5$ .................. G01N 21/64; G01N 33/64; C07C 205/00; C07C 229/00

[52] U.S. Cl. .................................. 436/128; 436/93; 436/94; 436/127; 436/129; 436/161; 436/162; 436/172; 549/438; 549/439; 560/21; 560/22; 560/45; 560/48; 562/435; 562/437; 562/452; 562/458

[58] Field of Search .................. 436/93, 94, 127, 128, 436/129, 161, 162, 172; 549/438, 439; 560/21, 22, 45, 48; 562/435, 437, 452, 458

[56] References Cited

U.S. PATENT DOCUMENTS

| | | | |
|---|---|---|---|
| 2,252,666 | 8/1941 | Reiff et al. | 562/435 X |
| 3,210,370 | 10/1965 | Ursprung | 560/22 X |
| 3,406,195 | 10/1968 | Taylor | 562/435 X |
| 3,565,943 | 2/1971 | Juby et al. | 560/48 X |
| 3,647,864 | 3/1972 | Ackermann | 562/435 |
| 3,931,303 | 1/1976 | Chang et al. | 562/437 X |
| 3,950,322 | 4/1976 | Thomas et al. | 260/210 R |
| 3,969,368 | 7/1976 | Manghisi et al. | 260/340.5 |
| 4,018,790 | 4/1977 | Paget et al. | 560/22 X |
| 4,314,936 | 2/1982 | Yaron et al. | 260/112.5 |
| 4,333,951 | 6/1982 | Walsh | 562/452 X |
| 4,684,371 | 8/1987 | Konrad et al. | 8/408 |
| 4,701,418 | 10/1987 | Katopodis | 436/93 X |
| 4,883,901 | 11/1989 | Elongo | 562/435 X |

FOREIGN PATENT DOCUMENTS

| | | |
|---|---|---|
| 0039455A1 | 11/1981 | European Pat. Off. . |
| 0273388A3 | 7/1988 | European Pat. Off. . |
| 474221 | 3/1929 | Fed. Rep. of Germany . |
| 2306289 | 10/1973 | Fed. Rep. of Germany . |
| WO81/00511 | 1/1991 | PCT Int'l Appl. . |

OTHER PUBLICATIONS

H. Goldstein et al. *Helv. Chim. Acta* 1957, 45, 369–372.
S. M. Aharoni et al. *J. Poly. Sci.: Poly. Chem. Ed.* 1974, 12, 639–650.
J. D. Roberts et al. "Basic Principles of Organic Chemistry" 2nd ed., 1977, W. A. Benjamin, Inc.; Menlo Park, Calif., pp. 817–818 & 1058–1064.
S. W. Shabaly et al. *J. Poly. Sci.: Poly. Chem. Ed.* 1974, 12, 2891–2903.
D. W. Dunwell et al. *J. Med. Chem.* 1975, 18, 692–694.
R. M. Silverstein et al. "Spectrometric Identification of Organic Compounds" 4th ed., John Wiley & Sons: New York, 1981, pp. 321–327.
D. W. Dunwell et al. *Chem. Abstr.* 1976, 84, No. 84:17279e.
S. Hara et al. *Chem. Pharm. Bull.* 1985, 33, 3493–3498.
T. Iwata et al. *Chem. Pharm. Bull.* 1985, 33, 3499–3502.
M. Nakamura et al. *Chem. Pharm. Bull.* 1987, 35, 687–692.

(List continued on next page.)

Primary Examiner—Jill A. Johnston
Assistant Examiner—Arlen Soderquist
Attorney, Agent, or Firm—Townsend and Townsend Khourie and Crew

[57] ABSTRACT

Compounds containing α-discarbonyl groups are rendered capable of fluorescent emission by conjugation with carboxylic acid-terminated ortho-diaminoaryl reagents. The carboxylic acid groups serve as ionizable moieties which facilitate the conjugation reaction, and are retained in the conjugation product to enable, or enhance the ability of, the conjugated compounds to be separated in chromatographic and electromigration separation processes, notably electrophoresis. Ortho-dinitro derivatives of the reagents are also disclosed, these derivatives offering the advantage of stability as well as the ability to be used directly in the reaction in the presence of a reducing agent.

31 Claims, 4 Drawing Sheets

OTHER PUBLICATIONS

S. Hara et al. *Anal. Chim. Acta* 1988, 215, 267–276.
A. E. Moormann *J. Med. Chem.* 1990, 33, 614–626.
S. Ohmori *J. Chromatogr.* 1991, 566, 1–8.
G. Slooff *Rec. Pay-Bas. Trav.* 1938, 57, 673–676.
G. Slooff *Rec. Trav. Chim* 1935, 54, 995–1010.
J. Böeseken et al. *Chem. Abstr.* 1935, 29, 2937a.
P. Ruggli et al., *Helv. Chim. Acta* 1946, 29, 1684–1688.
Y. Asahina et al. *Ber.* 1938, 71, 1421–1428.
W. Davies et al. *J. Chem. Soc.* 1922, 121, 2640–2655.
Z. Eckstein et al. *Chem. Abstr.* 1958, 52, abstract 9999a.
G. Berti et al. *Chem. Abstr.* 1961, 55, abstract 2536b.
Z. Eckstein et al. *Roczniki Chem.* 1964, 38, 51–59.
Z. Eckstein et al. *Chem. Abstr.* 1964, 60, abstract 14424b.
Hara, S., et al., "Highly Sensitive Determination of N-Acetyl-and N-Glycolylneuraminic Acids in Human Serum and Urine and Rat Serum by Reversed-Phase Liquid Chromatography with Fluorescence Detection," *Journal of Chromatography* 377, 111–119 (1986).

HIGHER M.W. FRACTION

FLUOROGENIC REAGENTS FOR DETECTION OF GLYCOCONJUGATES, α-KETOACIDS AND DIKETONES

This invention relates to fluorescence labeling techniques, and to materials and methods for the detection of α-dicarbonyl compounds.

BACKGROUND OF THE INVENTION

Sialic acids, such as N-acetylneuraminic acid (NANA), are α-ketoacids which occur as non-reducing terminal residues in the carbohydrate chains of glycoproteins and glycolipids. Abnormal levels of NANA have been detected in the serum and urine of cancer patients and of persons who are afflicted with certain congenital metabolic diseases. The early detection and quantitation of NANA thus offers a means of diagnosing various disease states and of providing early signals for the initiation of therapy.

The detection and measurement of sialic acid-terminated oligosaccharides has long presented a problem in biochemical investigations and routine analyses. The lack of detectable moieties which distinguish these molecules from other oligosaccharides has hindered developments in this area of glycobiology. Techniques for detection and quantitation of these molecules at early stages of their proliferation have been hampered by numerous problems, including lack of specificity of a derivatization reagent for α-keto acids or aldehydes, low sensitivity of the particular analytical technique employed, a lack of reagents which can be employed with highly polar analytes, and the instability of the derivatization reagents.

A spectrophotometric method of sialic acid determination using thiobarbituric acid has been employed, but this method lacks both selectivity and sensitivity. See, L. Warren, *J. Biol. Chem.* 234:1971 (1959) and D. Aminoff, *Virology* 7:355 (1959). Assays of NANA have also been performed as disclosed in the following publications: R. Schauer, *Methods Enzymol.* 50C:64 (1978), using gas chromatography (GC); I. Mononen, et al., *FEBS Lett.* 59:190 (1975), using gas chromatography-mass spectrometry (GC-MS); A. K. Shukla, et al., *J. Chromatogr.* 244:81 (1982) and H. K. B. Silver, et al., *J. Chromatogr.* 224:381 (1981), using high-performance liquid chromatography (HPLC) with UV detection; and S. Hara, et al., *J. Chromatogr.* 377:111–119 (1986), using HPLC with fluorescence detection. Both GC and HPLC with UV detection lack the sensitivity to detect NANA at picomole levels or below. Sensitivity is enhanced using GC-MS, but the cumbersome procedure for sample preparation limits the usefulness of this technique in rapid, diagnostic assays. The more recent method using HPLC with fluorescence detection involves the formation of a fluorescent quinoxaline from 1,2-diamino-4,5-dimethoxybenzene and NANA. This technique does not however permit the determination of highly polar analytes or provide for optimal reaction product behavior in electrophoresis and high-sensitivity fluorimetry. An additional problem is that the shelf life of the reagent employed is very limited.

SUMMARY OF THE INVENTION

The present invention resides in novel, stable fluorogenic reagents that make feasible the performance of high-sensitivity analyses of numerous biologically important compounds. The invention also resides in the synthesis and use of these reagents.

In one aspect, the present invention resides in fluorogenic reagents which contain two nitro groups in adjacent positions on an aromatic ring, the ring also bearing at least one substituent which includes a carboxylic acid. These dinitro compounds are stable and permit the in situ generation of the less stable diamino derivatives, which in turn react with α-ketoacids or α-diketones to form fluorescent quinoxalines. Incorporation of at least one carboxylic acid moiety into the fluorogenic reagent provides the added benefit of facilitating the reaction of the reagent with a highly polar analyte. A further benefit of carboxylic acid incorporation is that it enables, or enhances the ability of, the fluorescently tagged compounds to be separated by capillary electrophoresis and other forms of chromatography.

In another aspect, the present invention resides in the use of laser-induced fluorescence to detect and measure the product species. By appropriate selection of a fluorogenic reagent within the scope of this invention for reaction with an analyte of interest, one achieves a reaction product which is excitable to an optimal degree by lasers dedicated to certain wavelengths, such as a helium/cadmium laser or an argon/ion laser. For α-ketoacid analytes, the sensitivity of detection by this method extends below femtomole levels ($10^{-15}$ mole levels). For example, the method may be used for solutions having concentrations of $10^{-7}$M to $10^{-8}$M, with volumes injected being on the order of $10^{-9}$ L.

The compounds of the invention are further useful for the detection and quantitation of widely-occurring groups of neutral sugars possessing reducing ends, other naturally-occurring α-ketoacids and neurotoxic diketones. In the case of the neutral sugars, the reducing ends are oxidized to α-keto moieties prior to derivatization.

DETAILED DESCRIPTION OF THE INVENTION AND PREFERRED EMBODIMENTS

Figures 1A, 1B:
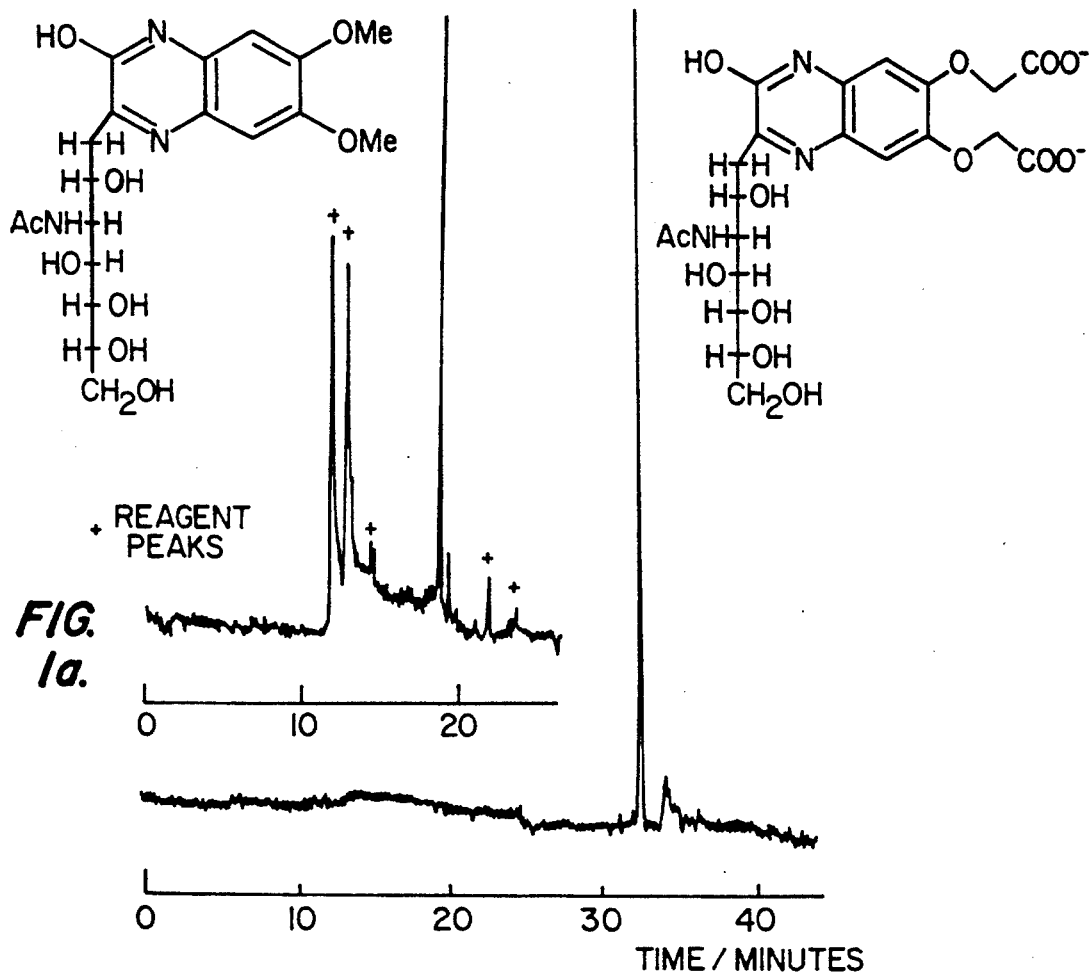
FIGS. 1, 2, 3 and 4 are detector traces of electropherograms of derivatized α-ketoacids, both singly and in mixtures, prepared in accordance with the present invention. These traces are the results of experiments reported in several of the examples herein, and are included as data of the efficacy and utility of the present invention.

The term "alkyl" is used herein in its conventional sense, including hydrocarbon radicals which are monovalent (one site of attachment) or polyvalent (two or more sites of attachment), either in a straight chain or branched chain, and may include sites of unsaturation (i.e., carbon—carbon double bonds and triple bonds). Preferred alkyl groups will contain 1–10 carbon atoms. All numerical ranges expressed in this specification are inclusive of their upper and lower limits.

The term "fluorescently tagged" refers to a sample analyte which has been chemically altered to contain a moiety which is fluorescent when irradiated by electromagnetic radiation at the appropriate wavelengths.

The term "fused polycyclic aromatic radicals" refers to radicals of two or more aromatic rings in which two or more carbon atoms are common to two adjoining rings. Examples of these radicals are naphthyl, phenanthryl and anthryl. The term is further intended to include rings containing heteroatoms, for example, quinolinyl and quinazolinyl.

The term "α-dicarbonyl-containing analyte" refers to a molecule which is to be analyzed and which contains two carbonyl groups which share a common bond. The two carbonyl groups may be in the form of an α-diketone, α-keto aldehyde or an α-keto acid.

Similarly, the term "α-dicarbonyl-containing analyte" refers to molecules as just described in which the two carbonyl groups make up either an α-keto aldehyde or an α-keto acid. These are often found at the end of a carbohydrate residue or glycoprotein. Examples of these analytes are N-acetyl neuraminic acid and α-ketoglutaric acid.

In its broadest sense, the present invention resides in the synthesis and use of novel fluorogenic reagents for the high-sensitivity determination of biologically important compounds. As indicated above, these reagents contain ionizable groups incorporated in their structures. The benefits of these groups are twofold. First, the α-dicarbonyl compounds which are to be determined are often highly polar components of an aqueous mixture. The use of reagents for fluorescence tagging with ionizable groups results in a homogeneous reaction which permits quantitative detection of the α-dicarbonyl species in the analyte. Second, the retention of the ionizable groups in the quinoxaline products permits these products to be easily separated from impurities through capillary electrophoresis or high-performance liquid chromatography in buffered aqueous solvent systems.

More particularly, the fluorogenic reagents of the present invention comprise ortho-dinitro and ortho-diamino compounds, represented by Formulae I and II, respectively.

$$O_2N\diagdown\diagup Ar\{R(CO_2H)_m\}_n \quad (I)$$
$$O_2N\diagup$$

$$H_2N\diagdown\diagup Ar\{R(CO_2H)_m\}_n \quad (II)$$
$$H_2N\diagup$$

In both Formula I and Formula II, the symbol "Ar" represents either a phenyl radical or a fused polycyclic aromatic radical, with the two $O_2N$ radicals at ortho-positions relative to each other. The symbol "R" represents a radical bonded to Ar through one or two single bonds, and is either alkyl, —O-alkyl,

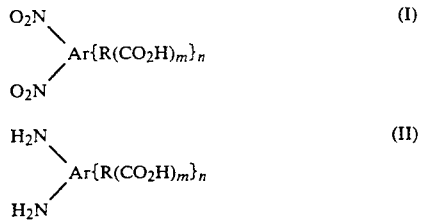

The indices m and n are each integers ranging from 1 to 4.

Certain embodiments within the scope of the description in the last paragraph are preferred. For example, the radical Ar is preferably phenyl, naphthyl, anthryl or phenanthryl, and most preferably phenyl or anthryl. The radical R is preferably a radical bonded to Ar through one or two single bonds, and alkyl groups within the definition of R are preferably $C_1$-$C_6$ alkyl and most preferably $C_1$-$C_4$ alkyl. A particularly preferred subclass is that in which R is either —O-($C_1$-$C_4$ alkyl) or

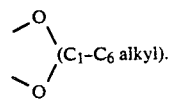

In still further preferred embodiments, m and n are each integers of 1 or 2 such that the product m×n is 1 or 2.

To use a fluorogenic reagent within the scope of this invention for the determination of a α-discarbonyl compound, the reagent is reacted with the compound to form a fluorescent quinoxaline, which is detectable by laser-induced fluorescence detection and other fluorometric techniques, at levels as low as the femtomole range and lower. One or more such quinoxalines thus formed are then capable of being chromatographically separated from any impurities present in the sample and irradiated with electromagnetic radiation for analysis for fluorescence emission. Reagents are in the form of ortho-dinitro species may be used to form the quinoxalines. This is accomplished by first converting the ortho-dinitro species to the corresponding ortho-diamino species which are then reacted with the α-discarbonyl containing analyte. This is conveniently done in a single reaction mixture without the isolation of the ortho-diamino intermediates. The quinoxalines, thus formed, are separated from other polar species, irradiated and analyzed for fluorescence emission.

In a preferred embodiment, the method of the invention involves detecting the presence of at least one α-discarbonyl containing analyte, which is present in a liquid sample at concentrations below about $10^{-6}M$, by contacting the analyte with the diamino form of the preferred fluorogenic reagents above. The diamino form of the reagents may be generated immediately prior to use by the reduction of the dinitro form using any of the wide variety of conventional reducing agents well known among those skilled in the art. Examples of suitable reducing agents are $NaBH_4/CuSO_4$, $H_2/Pd(C)$, and ammonium formate/Pd(C). The liquid sample containing the newly formed fluorescently tagged species, which is a quinoxaline, is subjected to analytical separation which may be capillary electrophoresis, high-performance liquid chromatography, slab gel electrophoresis, thin-layer chromatography, or any of the wide variety of known separation methods suitable for materials of this type. The separated species are then irradiated with a laser, which selectively excites the analytes of interest in an optimal manner and the species are then analyzed for fluorescence emission.

In a further preferred embodiment, at least one of the α-dicarbonyl species is an α-ketoacid or an α-keto aldehyde and at least one of these species is present in the liquid sample at a level in the range of $10^{-18}$ mole. The diamino fluorogenic reagent is formed immediately prior to use from the reduction of the dinitro precursor with $NaBH_4/CuSO_4$ and is used in solution. The fluorescently tagged species which is formed is either a quinoxaline or a 2-hydroxyquinoxaline and is separated on capillary electrophoresis. Irradiation of the fluorescent species is carried out with a laser dedicated to a wavelength at which the species are selectively excitable, and emission is monitored using a fluorescence detector.

The invention is particularly useful in the detection of terminal α-keto acids present in a sample at an amount of less than about $10^{-12}$ mole. In the practice of this invention, the sample is reacted with a solution of one of the diamino fluorogenic reagents of the invention. The resulting mixture is then subjected to capillary electrophoresis, irradiated with a helium/cadmium laser and monitored for fluorescence emission. Additionally, the fluorogenic reagents used are those which have been freshly prepared from dinitro precursors by reduction with $NaBH_4/CuSO_4$.

In all embodiments of the invention, conditions such as temperature, pressure, choice of solvent and concentration are not critical and may vary widely. Preferred ranges for temperature are from about 0° C. to about 100° C., with about 15° C. to about 45° C. being optimal. The preferred pressure for all aspects of the invention is atmospheric pressure, although those skilled in the art will recognize that some aspects, for example long-term storage of fluorogenic reagents, may be carried out at reduced pressure (i.e., storage in a vacuum dessicator). The preferred solvents are generally aqueous mixtures of common organic solvents, for example, water/methanol, water/acetonitrile and water/dimethylformamide. Chromatographic techniques used in the practice of the invention are conventional techniques well known among those skilled in the art.

The following examples are offered by way of illustration and not by way of limitation.

Examples 1 and 2 illustrate the two steps required for the synthesis of 4,5-dinitrocatechol-O,O-diacetic acid. Examples 3–6 illustrate the four steps involved in the synthesis of 2-(2-carboxyethyl)-5,6-dinitro-2-methylbenzodioxole. Examples 7–9 illustrate a semi-convergent synthetic route which may be used for the synthesis of 1,4-bis(carboxymethoxy)-7,8-diaminoanthracene. Example 10 illustrates a method by which the compounds of the present invention (including those compounds of Examples 2, 6 and 9) may be used for the detection and quantitation of α-discarbonyl containing analytes. Examples 11–14 illustrate the benefits and advantages of the invention.

EXAMPLE 1

Synthesis of 4-Nitrocatechol-O,O-diacetic Acid

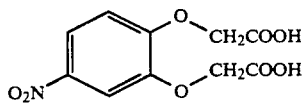

Catechol-O,O-diacetic acid (829 mg, 3.67 mmol from Lancaster Synthesis) was added gradually to 4.2 mL of 80% nitric acid which was cooled in an ice-salt bath. The mixture was stirred at below 0° C. for 2.5 h and 0°–10° C. for 1 h. The resulting homogeneous mixture was poured onto 25 g ice and the pasty precipitate was isolated by filtration, washed with water, dissolved in THF and dried over magnesium sulfate. Removal of solvent provided the desired product (623 mg, 2.30 mmol, 63% yield).

EXAMPLE 2

Synthesis of 4,5-Dinitrocatechol-O,O-diacetic Acid

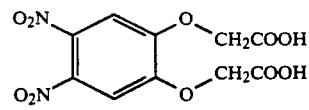

To 6.0 mL of 80% nitric acid, chilled in an ice-salt bath, was added in one portion 4-nitrocatechol-O,O-diacetic acid (623 mg, 2.30 mmol). The mixture was stirred 3 hr, warming gradually to 2° C., poured onto ice and filtered. The residue was washed with water and dried to provide 4,5-dinitrocatechol-O,O-diacetic acid (356 mg, 1.13 mmol, 49% yield).

EXAMPLE 3

Synthesis of 2-(2-Carbethoxyethyl)-2-methylbenzodioxole

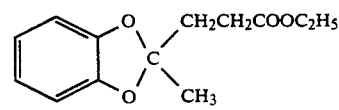

A mixture of catechol (2.44 g, 22.2 mmol), ethyl levulinate (2.99 mL, 21.1 mmol), xylenes (15 mL) and anhydrous cupric sulfate (443 mg, 2.78 mmol) was heated to reflux for 3 hr with continuous removal of water. Solvent was removed by distillation and the residue was dissolved in pentane, washed with 1M NaOH and saturated aqueous NaCl. The pentane solution was passed through Florisil to remove colored impurities, and dried with magnesium sulfate. Removal of solvent provided 2-(2-carbethoxyethyl)-2-methylbenzodioxole (2.85 g, 12.1 mmol, 57% yield).

EXAMPLE 4

2-(2-Carbethoxyethyl)-2-methyl-5-nitrobenzodioxole

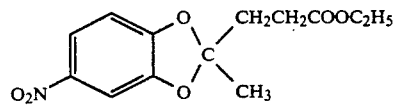

To 8.0 mL of concentrated nitric acid in an ice-salt bath was added 2-(2-carbethoxyethyl)-2-methylbenzodioxole (1.46 g, 6.20 mmol) while maintaining the temperature below 0° C. The mixture was stirred an additional 3 hr at below 0° C., poured onto ice (40 g) and extracted with methylene chloride. The organic phase was washed with saturated aqueous NaCl, aqueous sodium bicarbonate, then dried with $MgSO_4$. Solvent was removed to provide 2-(2-carbethoxyethyl)-2-methyl-5-nitrobenzodioxole (1.66 g, 5.92 mmol, 96% yield).

EXAMPLE 5

Synthesis of 2-(2-Carboxyethyl)-2-methyl-5-Nitrobensodioxole

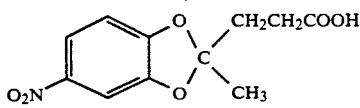

A solution of 2-(2-carbethoxyethyl)-2-methyl-5-nitrobenzodioxole (7.58 g, 27.0 mmol) in 30 mL of methanol was combined with a solution of potassium hydroxide (3.02 g, 54.0 mmol) in 10 mL of $H_2O$ and heated to reflux for 2 h. Solvent was removed and methylene chloride was added. The organic layer was separated and extracted with aqueous sodium bicarbonate. Careful acidification of the aqueous layer provided a yellow precipitate which was removed by filtration, washed with water and dried to leave 2-(2-carboxyethyl)-2-methyl-5-nitrobenzodioxole (4.49 g, 17.7 mmol, 66% yield).

EXAMPLE 6

Synthesis of 2-(2-Carboxyethyl)-5,6-dinitro-2-methylbenzodioxole

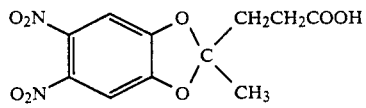

To 8.6 mL of 80% nitric acid in an ice-salt bath was added 2-(2-carboxyethyl)-2-methyl-5-nitrobenzodioxole (836 mg, 3.30 mmol). After 3 h, during which time the temperature rose to 0° C., ice (60 g) was added. The resulting precipitate was isolated by filtration, washed with water and dried to provide 2-(2-carboxyethyl)-5,6-dinitro-2-methylbenzodioxole (770 mg, 2.58 mmol, 78% yield).

EXAMPLE 7

Synthesis of 2,1,3-Benzoselenodiazole-5-carboxylic Hydrazide

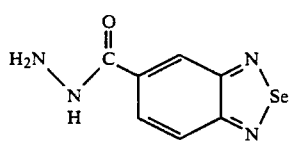

The synthesis of 2,1,3-benzoselenodiazole-5-carboxylic hydrazide may be accomplished by first treating 3,4-diaminobenzoic acid with selenium dioxide to form 2,1,3-benzoselenodiazole-5-carboxylic acid. Treatment of this product with methanol and sulfuric acid provides the ester which is subsequently converted to its acid hydrazide by treatment with hydrazine.

EXAMPLE 8

Synthesis of 3,6-Dimethoxysalicylic Aldehyde

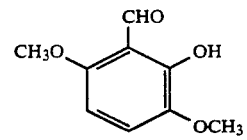

Treatment of 2,5-dimethoxybenzaldehyde with m-chloroperbenzoic acid provides, after workup, 2,5-dimethoxyphenol. Protection of the phenol can be accomplished by formation of a THP ether using dihydropyran and acid. Formylation of the resultant compound can be carried out using butyllithium and DMF. Subsequent acidification liberates the phenol to yield 3,6-dimethoxysalicylic acid.

EXAMPLE 9

Synthesis of 1,4-Bis(carboxymethoxy)-7,8-diaminoanthracene

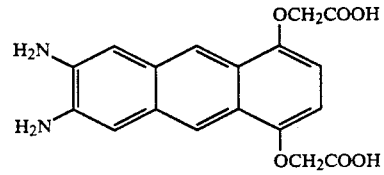

Synthesis of 1,4-Bis(carboxymethoxy)-7,8-diaminoanthracene may be accomplished by first combining 3,6-dimethoxysalicylic aldehyde with 2,1,3-benzoselenodiazole-5-carboxylic hydrazide. The resulting Schiff base can be treated with lead tetraacetate to provide 5-(2',5'-dimethoxy-6'-formylbenzoyl)-2,1,3-benzoselenodiazole. Oxidation of the formyl substituent can be accomplished using pyridinium dichromate. Subsequent reduction of the ketone may be carried out using Wolf-Kishner conditions ($N_2H_4 \cdot H_2O$/base). Removal of selenium to generate 6-(3',4'-diaminobenzyl)-2,5-dimethoxybenzoic acid is accomplished with borane dimethyl sulfide complex. Polyphosphoric acid cyclization produces the tricyclic nucleus which can be converted to 7,8-diamino-1,4-dimethoxyanthracene. Removal of the methyl groups with borane tribromide and subsequent alkylation with 2 equivalents of chloroacetic acid provides 1,4-Bis(carboxymethoxy)-7,8-diaminoanthracene.

EXAMPLE 10

Fluorescent Tagging of Analytes

The fluorescent tagging of a α-discarbonyl-containing analyte with the compounds of this invention may be achieved with either the diamino compounds or the dinitro compounds. When a diamino compound is used, the reaction should be conducted immediately following preparation. The dinitro precursors may be stored indefinitely and reduced to their diamino forms just prior to their contact with the analyte mixture. A typical reduction of a dinitro compound is as follows. The dinitro compound (1 mg) is dissolved in 10 μL of methanol and treated with 10 μL of a 2M aqueous $CuSO_4$ solution. Sodium borohydride (5 μL of a 5M solution) is added followed by additional portions of 10 μL of 2M $CuSO_4$ and 5 μL of 5M $NaBH_4$. After 10 min at ambient temperature, methanol (40 μL) is added and the mixture is centrifuged. The supernatant containing the diamino compound is drawn off and used directly.

Derivatization of an α-ketoacid is accomplished by treatment of the α-ketoacid (500 μg) with 10 μL of the diamino compound solution described above. Addition of 10 μL of 0.5N HCl provides a fluorescent derivative which may be analyzed using capillary electrophoresis together with laser-induced fluorescence detection.

EXAMPLE 11

Comparison of Two Fluorogenic Reagents

The dinitro compounds of the present invention have the added benefit of stability which leads to less interference during analysis than is observed with the use of the diamino compounds. FIG. 1 compares the results obtained using the 1,2-diamino-4,5-dimethoxybenzene described by Hara, et al., *J. Chromatogr.* 377:111–119 (1986) with those obtained using 4,5-dinitrocatechol-O,O-diacetic acid of the present invention. Derivatization of NANA from human α-1 acid glycoprotein with either 1,2-diamino-4,5-dimethoxybenzene or 4,5-dinitrocatechol-O,O-diacetic acid (which is reduced to the diamine in situ) provides the quinoxalines shown beside their respective electropherograms. The electropherograms were generated using laser-induced fluorescence detection following elution on a capillary column (50 μm×60 cm, 14 kv, 20 μA) with a buffer of 20 mM borate and 20 mM phosphate at pH 9.5.

EXAMPLE 12

Analysis of Polygalacturonic Acid Mixtures

Figure 2A:
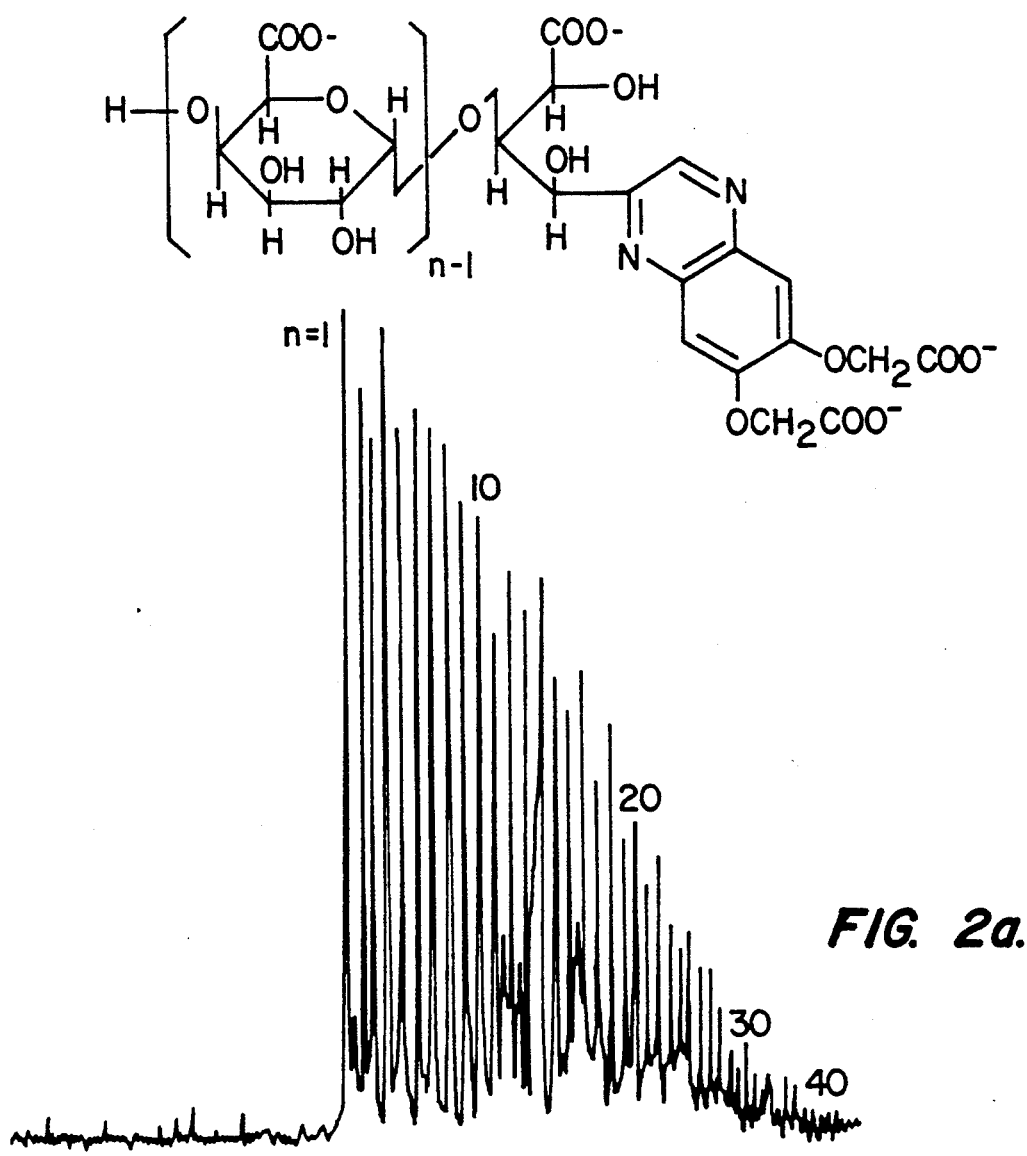
Figure 2B:
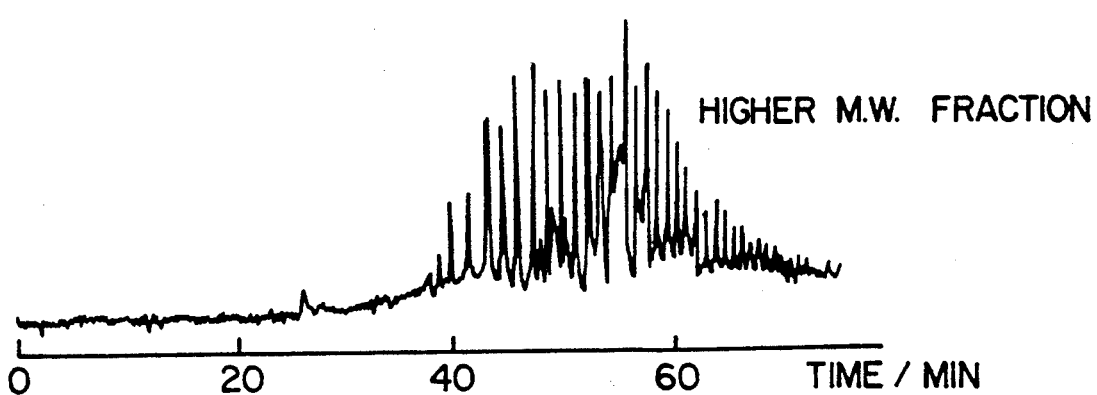

The method of the present invention may also be used for the analysis of complex mixtures of oligosaccharides. FIG. 2 illustrates the capillary electrophoresis separation of fluorescently tagged polygalacturonic acids.

EXAMPLE 13

Analysis of Two α-Ketoacids

Figure 3:
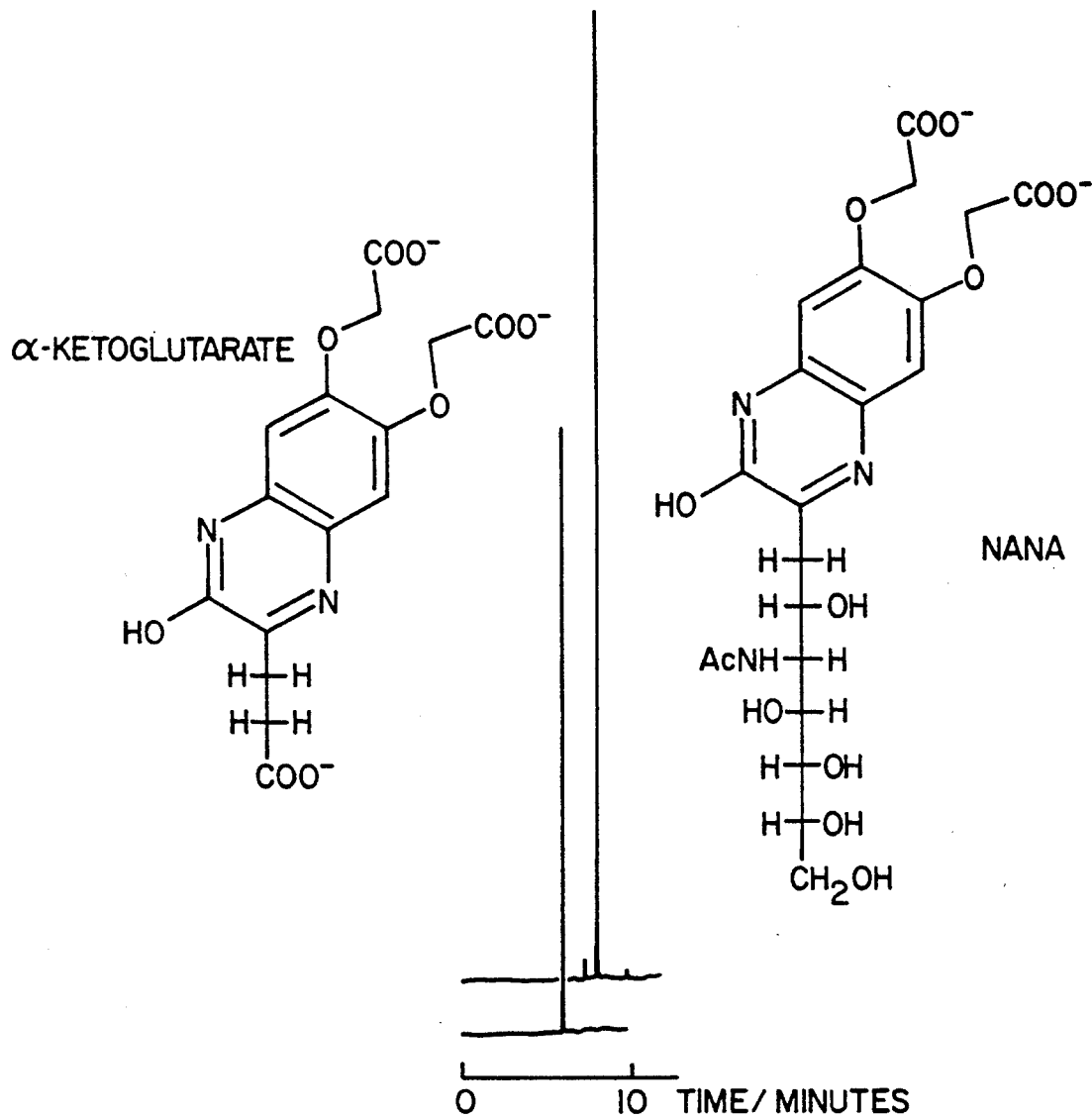

Contaminating α-ketoacids are readily separated and detected using the method of the present invention, as shown in FIG. 3. Capillary electrophoresis was run using a coated capillary column of 50 cm length with a 50 μm inside diameter, a buffer of 200 mM borate at pH 7.5 and 20 kv, 6 μA (voltage reversed). Fluorescence was detected at 452 nm following eluant irradiation with a He/Cd laser (325 nm). The electropherograms of quinoxalines derived from either α-ketoglutarate or NANA with diaminocatechol diacetic acid have been superimposed to demonstrate the difference in their respective migration times despite the similarity of their functional groups.

EXAMPLE 14

Determination of the Level of Detection Using Laser-Induced Fluorescence

Figures 4A, 4B:
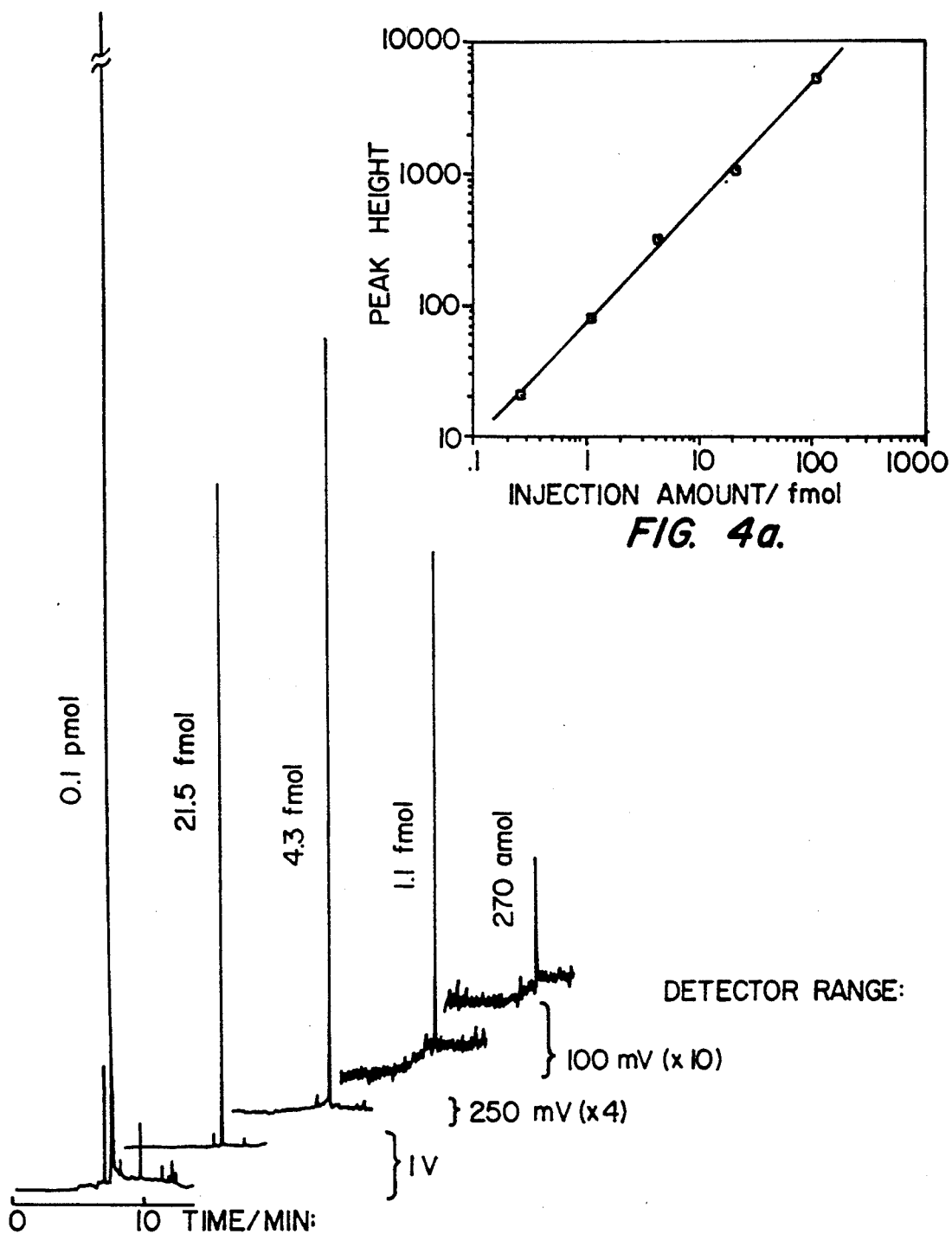

Using the method of the present invention, quinoxaline derivatives formed may be detected at below femtomole levels as shown in FIG. 4. The quinoxaline derivative formed by the treatment of NANA with 4,5-diaminocatechol-O,O-diacetic acid was subjected to He/Cd laser fluorescence detection following capillary electrophoresis on a coated capillary column using a buffer of 200 mM borate at pH 7.5 and 20 kv, 6 μA (voltage reversed). The quinoxaline was detected at levels of 0.27 fmol (two orders of magnitude below those observed by Hara, et al. in similar experiments).

The foregoing is offered primarily for purposes of illustration. It will be readily apparent to those skilled in the art that the molecular structures, operating conditions, materials, procedural steps and other parameters of the system described herein may be further modified or substituted in various ways without departing from the spirit and scope of the invention.

What is claimed is:

1. A method for detecting the presence of at least one α-dicarbonyl-containing analyte in a liquid sample, said method comprising:

(a) treating said sample with a compound having the formula

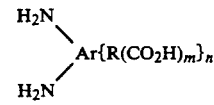

in which:
   Ar is an aryl radical selected from the group consisting of phenyl and fused polycyclic aromatic radicals, with the two $H_2N$ radicals shown in said formula bonded to Ar at ortho-positions relative to each other,
   R is a radical bonded to Ar through one or two single bonds, and is a member selected from the group consisting of —O—alkyl,

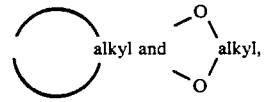

m is an integer of 1 to 4, and
   n is an integer of 1 to 4, wherein m×n is at least 2, to form fluorescently tagged derivatives of said at least one gem-dicarbonyl-containing analyte, said derivatives each containing at least one carboxylic acid group;

(b) passing said liquid sample so treated through a chromatographic separation medium to chromatographically separate components of said liquid sample from each other; and (c) detecting said fluorescently tagged derivatives among said components so separated, by fluorescence emission.

2. A method in accordance with claim 1 in which said at least one α-dicarbonyl-containing analyte is present in said liquid sample in an amount less than about $10^{-6}$ moles, and step (a) likewise comprises forming less than about $10^{-6}$ moles of said fluorescently tagged derivatives.

3. A method in accordance with claim 1 in which said at least one α-dicarbonyl-containing analyte is present in said liquid sample in an amount less than about $10^{-9}$ moles, and step (a) likewise comprises forming less than about $10^{-9}$ moles of said fluorescently tagged derivatives.

4. A method in accordance with claim 1 in which said at least one α-dicarbonyl-containing analyte is present in said liquid sample in an amount less than about $10^{-12}$ moles, and step (a) likewise comprises forming less than about $10^{-12}$ moles of said fluorescently tagged derivatives.

5. A method in accordance with claim 1 in which at least one of said α-dicarbonyl-containing analytes is a terminal α-dicarbonyl-containing analyte, and at least one of said fluorescently tagged derivatives of step (a) is a terminally fluorescently tagged derivative.

6. A method in accordance with claim 1 in which at least one of said α-dicarbonyl-containing analytes is an α-keto carboxylic acid, and step (a) comprises converting said at least one of said α-keto acids to a 2-hydroxyquinoxalinyl-containing species.

7. A method in accordance with claim 1 in which at least one of said α-dicarbonyl-containing analytes is a terminal α-keto carboxylic acid, and step (a) comprises converting said at least one of said terminal α-keto acids to a 2-hydroxyquinoxalinyl-containing species.

8. A method in accordance with claim 1 in which at least one of said α-dicarbonyl-containing analytes is an α-keto aldehyde, and step (a) comprises converting said at least one α-keto aldehyde to a quinoxalinyl-containing species.

9. A method in accordance with claim 1 in which at least one of said α-dicarbonyl-containing analytes is a terminal α-keto aldehyde, and step (a) comprises converting said at least one terminal α-keto aldehyde to a quinoxalinyl-containing species.

10. A method in accordance with claim 1 further comprising irradiating said sample, between steps (b) and (c), with electromagnetic radiation from a laser dedicated to a wavelength at which said fluorescently tagged derivatives are selectively excitable.

11. A method in accordance with claim 1 in which Ar of said compound of step (a) is a member selected from the group consisting of phenyl, naphthyl, anthryl and phenanthryl.

12. A method in accordance with claim 1 in which m and n of said compound of step (a) are such that the product m×n is 2.

13. A method in accordance with claim 1 in which R of said compound of step (a) is a member selected from the group consisting of —O—($C_1$–$C_6$ alkyl),

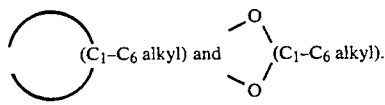

14. A method in accordance with claim 1 in which R of said compound of step (a) is a member selected from the group consisting of —O—($C_1$–$C_4$ alkyl) and

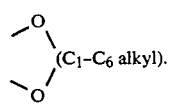

15. A method in accordance with claim 1 in which said compound of step (a) has the formula

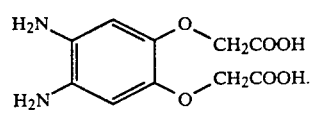

16. A method in accordance with claim 1 in which said compound of step (a) has the formula

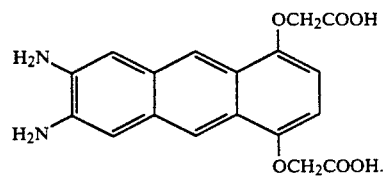

17. A compound having the formula

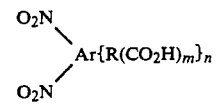

in which:
Ar is an aryl radical selected from the group consisting of phenyl and fused polycyclic aromatic radicals, with the two $O_2N$ radicals shown in said formula bonded to Ar at ortho-positions relative to each other;
R is a radical bonded to Ar through one or two single bonds, and is a member selected from the group consisting of —O—alkyl,

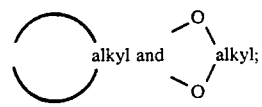

m is an integer of 1 to 4, and n in an integer of 1 to 4, wherein m×n is at least 2.

18. A compound in accordance with claim 17 in which Ar is a member selected from the group consisting of phenyl, naphthyl, anthryl and phenanthryl.

19. A compound in accordance with claim 17 in which Ar is a member selected from the group consisting of phenyl and anthryl.

20. A compound in accordance with claim 17 in which R is —O—alkyl.

21. A compound in accordance with claim 17 in which R is —O—($C_1$–$C_6$ alkyl).

22. A compound in accordance with claim 17 in which R is —O—($C_1$–$C_4$ alkyl).

23. A compound in accordance with claim 17 having the formula

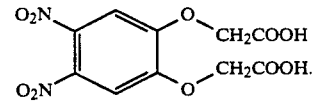

24. A compound in accordance with claim 17 having the formula

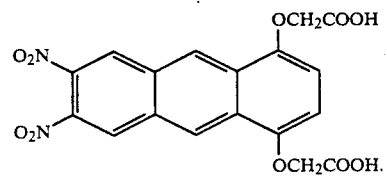

25. A compound having the formula

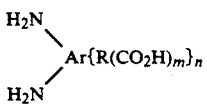

in which:
- Ar is an aryl radical selected from the group consisting of phenyl and fused polycyclic aromatic radicals, with the two H$_2$N radicals shown in said formula bonded to Ar at ortho-positions relative to each other;
- R is a radical bonded to Ar through one or two single bonds, and is a member selected from the group consisting of —O—alkyl,

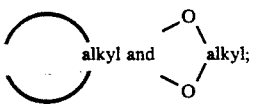

m is an integer of 1 to 4, and
n in an integer of 1 to 4,
wherein m×n is at least 2.

26. A compound in accordance with claim 25 in which Ar is a member selected from the group consisting of phenyl, naphthyl, anthryl and phenanthryl.

27. A compound in accordance with claim 25 in which Ar is a member selected from the group consisting of phenyl and anthryl.

28. A compound in accordance with claim 25 in which R is —O—alkyl.

29. A compound in accordance with claim 25 in which R is —O—(C$_1$-C$_6$ alkyl).

30. A compound in accordance with claim 25 having the formula

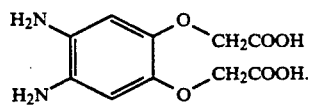

31. A compound in accordance with claim 25 having the formula

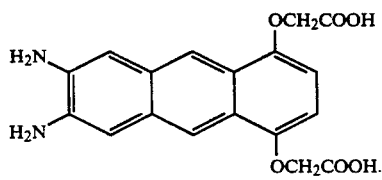

* * * * *

UNITED STATES PATENT AND TRADEMARK OFFICE
CERTIFICATE OF CORRECTION

PATENT NO. : 5,310,682
DATED : May 10, 1994
INVENTOR(S) : Milos V. Novotny, Osamu Shirota, Donald Wiesler It is certified that error appears in the above-indentified patent and that said Letters Patent is hereby corrected as shown below:

Column 1, line 5, --This invention was made with government support under the National Institutes of Health grant ROL GM 24349. The government has certain rights in the invention. --

Signed and Sealed this

Twenty-fourth Day of October, 1995

Attest:

BRUCE LEHMAN

Attesting Officer

Commissioner of Patents and Trademarks